United States Patent [19]

Silvian

[11] Patent Number: 4,991,583
[45] Date of Patent: Feb. 12, 1991

[54] PACEMAKER HAVING INDEPENDENTLY PROGRAMMABLE ELECTRODE CONFIGURATION FOR PACING AND SENSING AND METHOD FOR OPERATION THEREOF

[75] Inventor: Sergiu Silvian, Pasadena, Calif.

[73] Assignee: Siemens-Pacesetter, Inc., Sylmar, Calif.

[21] Appl. No.: 345,590

[22] Filed: May 1, 1989

Related U.S. Application Data

[63] Continuation-in-part of Ser. No. 896,542, Aug. 13, 1986, abandoned.

[51] Int. Cl.⁵ .............................................. A61N 1/368
[52] U.S. Cl. .............................................. 128/419 PG
[58] Field of Search .............................. 128/419 PG

[56] References Cited

U.S. PATENT DOCUMENTS

| | | | |
|---|---|---|---|
| 4,402,322 | 9/1983 | Duggan | 128/419 PG |
| 4,498,478 | 2/1985 | Bourgeois | 128/419 PG |
| 4,543,956 | 10/1985 | Herscovici | 128/419 PG |
| 4,549,548 | 10/1985 | Wittkampf et al. | 128/419 PG |
| 4,558,702 | 12/1985 | Barrenas et al. | 128/419 PG |
| 4,741,342 | 5/1988 | Stotts | 128/419 PG |

*Primary Examiner*—William E. Kamm
*Attorney, Agent, or Firm*—Lisa P. Weinberg; Leslie S. Miller

[57] ABSTRACT

A pacemaker and a method of operation thereof are provided for configuring or operating a conventional pacemaker having a plurality of lead electrodes. Each lead can be independently configured for any combination of unipolar or bipolar, pacing and sensing. During a pacing mode of operation, a selected return electrode is switchably connected to the most positive battery potential, $V_{DD}$. The return electrode of the packemaker, can selectively be either the pacemaker case or one or more ring electrodes. During a fast discharge time period, which occurs immediately subsequent to the delivery of a pacing pulse, the return electrode is disconnected from $V_{DD}$ and connected to the proximal side of a coupling capacitor through which the pacing pulse has passed. Also during this fast discharge time period, the proximal side of the coupling capacitor is switchable connected to the most negative battery potential, $V_{SS}$. During sensing, one input of the sensing amplifier is connected to either the tip electrode or the ring electrode. A second input of the sensing amplifier is switchably connected to the selected return electrode, either the case or the ring electrode. Sensing can therefore occur between tip electrode and ring electrode, tip electrode and case, or ring electrode and case. Furthermore, the case electrode is switchably connected to −0.5 volts during the sensing phase of operation.

45 Claims, 4 Drawing Sheets

| SENSING CONFIGURATION | ATRIAL | | | | VENTRICLE | | | |
|---|---|---|---|---|---|---|---|---|
| | P22 | P23 | P24 | P25 | P22' | P23' | P24' | P25' |
| A, UNIPOLAR TIP | X | | | X | | | | |
| A, UNIPOLAR RING | | X | | X | | | | |
| A, BIPOLAR | X | | X | | | | | |
| V, UNIPOLAR TIP | | | | | X | | | X |
| V, UNIPOLAR RING | | | | | | X | | X |
| V, BIPOLAR | | | | | X | | X | |

FIG. 5   X = TRANSISTOR SWITCH ON

PACEMAKER HAVING INDEPENDENTLY PROGRAMMABLE ELECTRODE CONFIGURATION FOR PACING AND SENSING AND METHOD FOR OPERATION THEREOF

CROSS-REFERENCE TO RELATED PATENT APPLICATION

This is a continuation-in-part of copending application Ser. No. 06/896,542, filed Aug. 13, 1986, now abandoned.

BACKGROUND OF THE INVENTION

The present invention relates to implantable pacemakers capable of pacing and sensing in at least one chamber of the heart. More particularly, the present invention, relates to a programmable dual chamber pacemaker wherein the basic configuration of the pacemaker, e.g., unipolar or bipolar, can be changed, including the grounding configuration and ground potentials used within the pacemaker.

Generally, a heart stimulator, commonly known as a "pacemaker" or "pacer," uses one or two flexible leads having one end connected to the pacer and the other end connected to electrodes placed in close proximity to the heart. These leads are used to stimulate or pace the heart. Also, these leads are used to sense the heart activity by picking up electrical signals from the heart.

In order to properly pace or sense, the pacer has to be able to deliver a stimulating pulse to the heart or sense an electrical signal from the heart, and this requires that there be an electrical return path. If, within a given heart chamber, a unipolar lead is used—containing a single conductor—the return path is the conductive body tissue and fluids. The return path is connected to the pacer by connecting the pacer electrical common or ground to the pacer metal enclosure, typically referred to as the pacer "case." The case, in turn, makes contact with the body tissue and/or fluids.

An alternative solution to using a unipolar lead in a given heart chamber is to use a double lead/electrode in the heart chamber, known as a bipolar lead. In a bipolar lead, a second conductor is spiraled over and insulated from a first conductor along the length of the lead. At the distal end of the lead, one of the conductors is connected to a first electrode, referred to as the "tip" electrode, and the second conductor is connected to a second electrode, referred to as a "ring" electrode. The ring electrode is generally situated 10 to 20 mm from the tip electrode. The tip electrode is typically placed in contact with heart tissue, while the ring electrode is in electrical contact with the blood. Because both body tissue and fluids are conductive, the ring electrode of a bipolar lead, in contact with the body fluids, serves as an electrical return for both pacing and sensing.

As indicated, pacing or sensing using the pacer case or enclosure as part of the electrical return path is known as unipolar pacing or sensing. Pacing or sensing using the lead ring electrode and associated lead conductor as the electrical return path is known as bipolar pacing or sensing.

There are numerous factors to consider when deciding whether unipolar or bipolar pacing and/or sensing should be used. Bipolar pacing has, in general, the advantage of requiring less energy than unipolar pacing. Further, bipolar sensing is less prone to crosstalk and myopotential sensing than is unipolar sensing. (Crosstalk, for purposes of this application, refers to a pacer mistakenly sensing a heart activity in one heart chamber immediately after the other chamber is paced.) Bipolar sensing reduces crosstalk resulting from a pacing stimulus in the opposite chamber. Bipolar pacing is preferred if pectoral stimulation occurs with uniploar pacing or if a pocket infection occurs around the unipolar case electrode.

Unipolar pacing and sensing offers the advantage, in general, of simpler circuitry within the pacemaker and a smaller diameter lead. Some doctors prefer unipolar over bipolar pacing and/or sensing as a function of other implantation and heart conditions. Depending on the lead orientation, unipolar sensing may be better than bipolar sensing. Furthermore, unipolar stimulation may be preferred if diaphragmatic stimulation occurs with bipolar pacing. Usually, the pacer has a unipolar factory-set configuration, but in the last five years some programmable configuration pacers have appeared.

In addition to the conventional unipolar and bipolar sensing configurations, a new sensing configuration has the potential of reducing even more the likelihood of crosstalk. This new configuration utilizes unipolar pacing in both channels, and senses between the ring electrode and the case. See U.S. Pat. No. 4,686,988, entitled "Pacemaker System and Method for Measuring and Monitoring Cardiac Activity and for Determining and Maintaining Capture", by Jason Sholder. Unipolar sensing from ring-to-case has all the advantages of unipolar sensing from tip-to-case, with the added benefit of reduced crosstalk due to its separation distance from the stimulation site. Not only is the crosstalk smaller with this new configuration, but one can readily determine capture just immediately after pacing (capture is defined as the heart contracting as a result of a pacer-delivered stimulus.)

As the number of configuration options and their combinations increases, especially with respect to dual chamber pacers (those designed to pace and/or sense in both chambers of the heart), it is clear that pacing and sensing programmability is very important. However, because a pacer is a low voltage, low power consumption device, the implementation of the switching circuitry needed to realize the different pacing and sensing configurations is very difficult. To illustrate, in order to have a very low power consumption device, pacers use integrated circuits with CMOS digital circuits and MOS analog switches and amplifiers. Further, low voltage, power and polarity requirements dictate the use of a P-well CMOS process. (A pacer is typically a positive ground system inasmuch as negative pacing pulses must be generated.) A difficulty with this CMOS process, and the resulting CMOS currents, is that no input, output or any internal transistor drain or source can go above $V_{DD}$ or below $V_{SS}$, where $V_{DD}$ is the positive supply voltage and $V_{SS}$ is the negative supply voltage. (For a single battery configuration, $V_{DD}$ is thus usually obtained from the positive battery terminal, and $V_{SS}$ from the negative battery terminal.) Because the battery of a pacemaker is typically a single 2.8 volt (V) lithium cell, whose voltage may decrease over its life to as low as 2.0V, this limitation makes it extremely difficult to design pacemaker circuits that will work properly in all output (pacing) and sensing configurations.

In a typical design, the pacer electrical common, or ground reference, is connected to the positive terminal of the battery. In turn, this ground reference is connected to the CMOS IC substrate. The negative terminal of the battery, which for a typical design is −2.8V, thus provides the $V_{SS}$ supply voltage for the pacer circuits. As pacing magnitudes greater than 2.8V are often required, a voltage adjusting circuit is used in conjunction with a storage capacitor for each channel of the pacemaker in order to produce these higher magnitude voltages. Also, such voltage adjusting circuits, or equivalent, can be used to produce some other higher magnitude voltages needed for circuits which have node voltages of greater magnitude than −2.8V.

However, even though voltage adjusting circuits can be used to produce needed voltages of greater magnitude than is available from the battery, a major problem still exists for nodes having voltages going above $V_{DD}$ or ground. An example will illustrate how such voltages occur. A pacer delivers a stimulating current pulse by switchably connecting the electrode tip, through a coupling capacitor, to the negative terminal of a storage capacitor, the positive terminal of this capacitor being grounded. The voltage stored on this storage capacitor has previously been adjusted or amplified to the desired magnitude by a voltage adjusting circuit. A coupling capacitor is required to prevent DC current from flowing through the tip electrode body interface. The return path for the pacing pulse is provided by grounding the case or ring electrode for unipolar or bipolar pacing, respectively. After delivering the pulse, the coupling capacitor remains charged with a positive charge on its tip electrode side (distal side). The pacer side of the coupling capacitor (proximal side) would likewise have a charge remaining thereon, but this charge is removed by connecting it through a discharging resistor (or switch) to ground. If, after pacing, it is desired to sense bipolarly between tip and ring, switching means must be used to connect the two inputs of a differential amplifier to the tip and ring electrodes. However, the tip potential remains above ground and the ring potential, situated in close proximity to the tip, has a potential somewhere between ground potential and the tip potential, but definitely above ground. As mentioned, no solid state switch of the type employed in pacer circuits (e.g., CMOS switch) can go above ground. Hence, a problem exists of how to switchably connect the positive (above ground) potentials of the tip and ring electrodes to the sense amplifier.

One possible solution to this problem is to connect the sensing amplifier to the proximal (negative) side of the coupling capacitor, which proximal side will have a potential below ground due to the discharge current through the discharging resistor or switch. This approach has the drawback, however, of applying the capacitor's discharging voltage slope to the sensing amplifier. Further, the ring electrode would have to be connected through an additional coupling capacitor in order to eliminate its voltage potential above $V_{DD}$ (ground). Requiring an additional discrete component, such as a capacitor, is very undesirable.

A further possible solution to this switching problem would be to have the system ground different from $V_{DD}$, e.g., midway between $V_{DD}$ and $V_{SS}$. However, doing so would require a midway voltage source, to produce the midway ground potential, that is buffered by a low output impedance buffer to sustain the high current demands of pacing. Alternatively, the system ground could be connected to −2.8V, the negative battery potential. However, doing so would require at least one more stage to the voltage adjusting circuit in order to produce the negative voltages required for pacing. The addition of such additional circuitry is undesirable because it would increase the bulk and power consumption of the pacer, as well as decrease its reliability.

SUMMARY OF THE INVENTION

In accordance with the present invention, a method of operation and an apparatus is provided for independently configuring one or both channels of a conventional pacer to either a unipolar or bipolar pacing mode of operation and either a unipolar tip-to-case, unipolar ring-to-case, or a bipolar tip-to-ring sensing mode of operation, despite positive potentials that appear at the tip or ring electrodes. Further, a fast discharge circuit is employed in order to rapidly discharge a coupling capacitor through which the pacing pulse is delivered to a tip electrode. This fast discharge circuit switchably disconnects the selected return electrode from positive battery potential and connects the coupling capacitor to both: (1) the case terminal or ring terminal (unipolar or bipolar, respectively), and (2) the negative battery potential for a prescribed time period subsequent to the delivery of the pacing pulse. In still a further embodiment, this fast discharge time period is followed by a slow discharge period wherein the coupling capacitor is connected to the case terminal or ring terminal (unipolar or bipolar, respectively) through a discharge resistor.

It is a feature of the present invention to provide a new method of sensing: unipolar sensing from a ring electrode to the case. It is further to provide a sensing amplifier which is configurable in all three modes of operation: unipolar sensing from the tip electrode to the case, bipolar sensing from the tip electrode to the ring electrode, or unipolar sensing from the ring electrode to the case. Such sensing is advantageously realized without the need of any additional coupling capacitors in the ring electrode sensing circuit. Further, this new mode provides all the benefits of unipolar sensing with the added advantage of reduced crosstalk and the ability to detect capture following stimulation.

A further feature of the present invention provides a pacemaker and a method of operation which paces and/or senses in unipolar or bipolar modes of operation wherein the selected return electrode (either the pacemaker case or the ring electrode) is switched from the positive battery potential during pacing to a slightly more negative potential, e.g., from −0.2 to −1.0 volts, during sensing. In accordance with one embodiment thereof, a fast discharge phase follows the pacing phase of operation wherein the return electrode is further connected to a third potential, $V_{SS}$. During this fast discharge phase, the coupling capacitor (through which the pacing pulse is delivered to the tip electrode) is switchably connected to both: (1) the case terminal (unipolar operation) or the ring terminal (bipolar operation), and (2) the negative battery potential, $V_{SS}$, for a short time period, thereby causing the coupling capacitor to rapidly discharge. This fast discharge phase may be followed by a slow discharge phase. During this slow discharge phase, the coupling capacitor is switchably connected to either the case (unipolar) or ring (bipolar) terminals through a resistor.

Advantageously, all of the switching and resulting connections used to achieve the above configurations are realized using low power solid state switching devices, such as CMOS devices, that are controlled by appropriate state and timing signals. These state and timing signals, for the most part, are the same signals that are generated and used in a conventional programmable pacemaker. Such signals are digital signals, and as such, can be readily stored in the memory circuits of the pacemaker, or easily generated from control signals stored in such memory circuits, and recalled or generated as needed. Further, such signals can be easily altered or changed, using known telemetry and programming techniques, in order to allow the configuration of the pacer to be set to a desired configuration.

BRIEF DESCRIPTION OF THE DRAWINGS

The above and other features and advantages of the present invention will be more apparent from the following more particular description thereof, presented in conjunction with the following drawings, wherein:

FIG. 5 is a table that defines the sensing configuration realized by the circuit of FIG. 4 as a function of the switches that are closed.

DETAILED DESCRIPTION OF THE INVENTION

Figure 1:
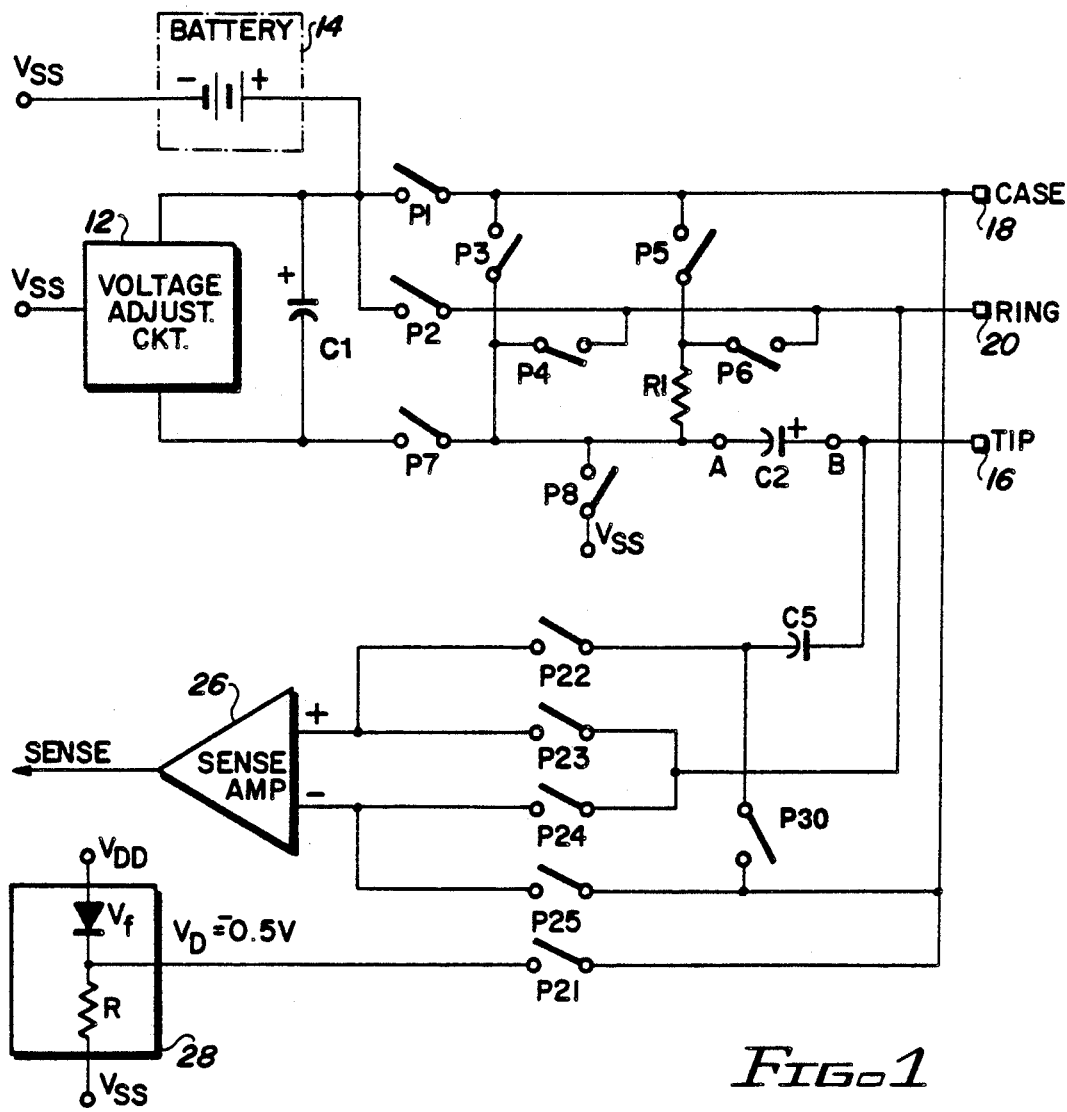
FIG. 1 is a simplified schematic diagram depicting one channel of the pacing and sensing circuits of the present invention.

The following description is of the best presently contemplated mode of carrying out the invention. This description is not to be taken in a limiting sense but is made for the purpose of describing the general principles of the invention. The scope of the invention should be determined with reference to the appended claims.

In the description that follows, when reference is made to the elements or parts of the invention shown in the drawings, like numerals will be used to refer to like parts throughout.

Referring first to FIG. 1, a simplified schematic diagram is shown of the pacing and sensing circuits of the present invention as used with one chamber of the heart. This figure will be used to teach the operating principles of the invention. A more detailed schematic diagram of the circuits of the invention can be found in FIGS. 3 and 4.

In FIG. 1, the basic pacing circuit includes a voltage adjusting circuit 12 and a storage capacitor C1. As it is known to one of ordinary skill in the art, a simple voltage adjusting circuit is a voltage multiplier, which is a circuit which charges capacitors in parallel and discharge them in series, effectively multiplying the battery voltage any number of times. Another implementation of a voltage adjusting circuit is a "charge pump" circuit. A charge pump circuit charges a number of capacitors from the battery source in one phase and connects them in series to an output capacitor in a subsequent phase, thereby obtaining any desired output voltage larger or lower than the battery voltage.

In a stimulation device, such as a pacemaker, it is desirable for the physician to program the desired magnitude of the stimulation pulse, since the threshold for capturing the heart varies from patient to patient. The stimulation pulse of desired magnitude is then delivered to a tip electrode terminal 16 by closing switch P7. The tip electrode terminal 16 is, in turn, connected to the tip electrode of a conventional pacing lead, not shown, thereby enabling the pacing pulse to be delivered to the heart. The return path for the stimulating pulse is provided either through the case terminal 18, for unipolar pacing, or the ring electrode terminal 20, for bipolar pacing. If unipolar pacing is selected, switch P1 is closed. If bipolar pacing is selected, switch P2 is closed.

Regardless of whether unipolar or bipolar pacing is selected, the pacing pulse must be delivered to the tip electrode terminal 16 through coupling capacitor C2. Capacitor C2 is needed in order to block DC currents from flowing from the storage capacitor C1 to the tip electrode terminal 16 and through the body tissue. It is noted that, as configured in FIG. 1, the pulse that is generated by closing switches P7 and P1 or P2 is a negative pulse relative to the pacer ground potential, $V_{DD}$. Generating a negative stimulation pulse in this or equivalent fashion is a requirement dictated by the physiology of the body and heart of the patient using the pacemaker. Hence, the pacemaker, during the pacing mode of operation, must essentially operate as a positive ground system if such a negative stimulation pulse is to be efficiently generated using a single battery 14. Further, because capacitor C2 has essentially a zero voltage across its terminals before a stimulation pulse and a negative stimulation pulse is required to stimulate cardiac tissue, capacitor C2 is charged such that side 22 thereof retains a positive charge after the pacing pulse has passed therethrough.

In order to remove any residual charges from the proximal side 24 of capacitor C2 before the delivery of the next pacing pulse, and thereby prevent any such charges from adversely affecting the magnitude of the pacing pulse that is delivered, switch P3 (unipolar operation) or switch P4 (bipolar operation) creates a discharge path from the proximal side 24 of capacitor C2 to either the case terminal 18 (unipolar operation) or ring terminal 20 (bipolar operation) for a short period of time termed the "fast discharge" period. This fast discharge period immediately follows the delivery of the pacing pulse to the tip electrode. During this fast discharge period, switch P8 further connects side 24 of capacitor C2 to the negative battery potential $V_{SS}$. After the fast discharge period, in order to ensure that essentially all the charge is removed from side 24 of capacitor C2, a slow discharge path is provided through resistor R1 and switch P5 (unipolar operation) or switch P6 (bipolar operation) to a bias potential of $-0.5$ volts. This bias potential is established by connecting the case electrode to a bias potential generated by voltage generator 28. Through this connection and the bulk conductance of the heart, the resting potential of the case, ring, and tip electrode will be $-0.5$ volts. Hence, by the time the next pacing pulse needs to be generated, essentially all of the charge will have been removed from capacitor C2, thereby allowing a pacing pulse of known magnitude to be delivered to the tip electrode terminal 16. Hence, it can be seen that by connecting the return electrode to $V_{SS}$ during the fast discharge phase and to $-0.5$ volts during the slow discharge phase, overvoltages generated during these phases are limited to potentials below ground, thereby protecting the switches controlling these electrodes.

Still referring to FIG. 1, sensing is realized by selectively connecting the two inputs of a conventional sense amplifier 26 to the desired combination pairs of the tip electrode terminal 16, the ring electrode terminal 20, or the case electrode terminal 18. If conventional unipolar sensing is desired, the tip electrode 16 is connected to the positive terminal of sense amplifier 26 by closing switch P22; and the negative terminal of sense amplifier 26 is connected to the case terminal 18 by closing switch P25. If bipolar sensing is desired, the positive terminal of sense amplifier 26 is connected through switch P22 to the tip electrode 16, as with unipolar pacing, but the negative terminal of sense amplifier 26 is connected to the ring electrode through switch P24. If the new sensing mode (that is, unipolar sensing from the ring to the pacemaker case) is desired, then the positive terminal of sense amplifier 26 is connected to the ring electrode 20 by closing switch P23, and the case electrode 18 is connected to the negative terminal of sense amplifier 26 through switch P25. It is noted that all switches remain open unless specifically closed, thereby preventing two signals from being applied to the same amplifier terminal at the same time. It is also noted that a coupling capacitor C5 is inserted in series with switch P22. This coupling capacitor C5 prevents the DC voltage component of any positive voltages that may be present on the tip electrode 16 from adversely affecting the operation of switch P22 or the other CMOS circuits and devices employed. In this configuration, a similar coupling capacitor is not required for the ring electrode, advantageously eliminating a component. It is further pointed out, that since the pacing return electrode is disconnected during the sensing period, pacing can be independently programmed to unipolar or bipolar pacing in either channel and sensing can be independently programmed in either channel to any of the three sensing modes described above.

Most significantly, the sensing circuits shown in FIG. 1 include switch P21 that connects a different reference potential, other than $V_{DD}$, to the case 18 during the sensing operation. In the preferred embodiment, this different reference potential is −0.5 volts, and is generated by voltage reference generator circuit 28. It is noted that while −0.5 volts is the preferred voltage for connecting the case during sensing, it is only representative of one of a range of voltages that could be so used. For example, any voltage lying within the range of −0.2 to −1.0 volts could be used for this same purpose. Advantageously, −0.5 volts corresponds to the forward voltage of a diode, and the current demands during the sensing mode of operation are light, the circuitry of the reference generator 28 can be very simple, such as a voltage divider network comprised of a resistor and a signal diode. In the preferred embodiment, the reference generator 28 includes a resistor 15 connected to $V_{ss}$ at one end and to the cathode of a signal diode 17 at the other end. The anode of the signal diode is connected to $V_{dd}$. Due to the forward voltage, Vf, of signal diode 17, the reference voltage, Vo, is approx. −0.5 volts. One would also know to substitute this reference generator with other known circuits. Using this additional reference voltage as the case reference during sensing in this fashion assures that any slight positive voltages that may be present on the tip or ring electrodes immediately following a stimulation pulse will not exceed the $V_{DD}$ potential applied to the substrate of the solid state switches that are used.

It is possible that following a stimulation pulse and fast discharge, some voltage will remain on capacitors C2 and this voltage could saturate the sensing circuits 26. It is noted that the coupling capacitor C5 is used to prevent such saturation from occurring by blocking the voltage remaining on capacitor C2 to switch P22. To further balance the charge on capacitor C5, a short auto zero pulse of approximately 100 microseconds is used, just after the end of the fast discharge period, to charge capacitor C5 through switch P30 and switch P21 to −0.5 volts in a sample and hold fashion. Following this autozero pulse, the case electrode 18 and the ring electrode 20 (through bulk conductance) are also connected to −0.5 volts. Therefore, all of the switch voltages remain biased around −0.5 volts during sensing. This sensing configuration prevents any switch voltage from going above $V_{DD}$.

Figure 2A:
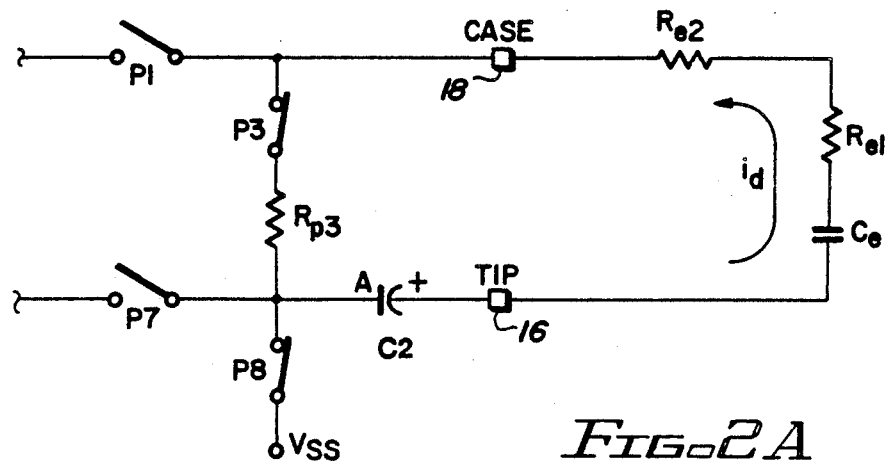
FIG. 2A is an equivalent circuit diagram of the circuit of FIG. 1 during the fast discharge time period.
Figure 2:
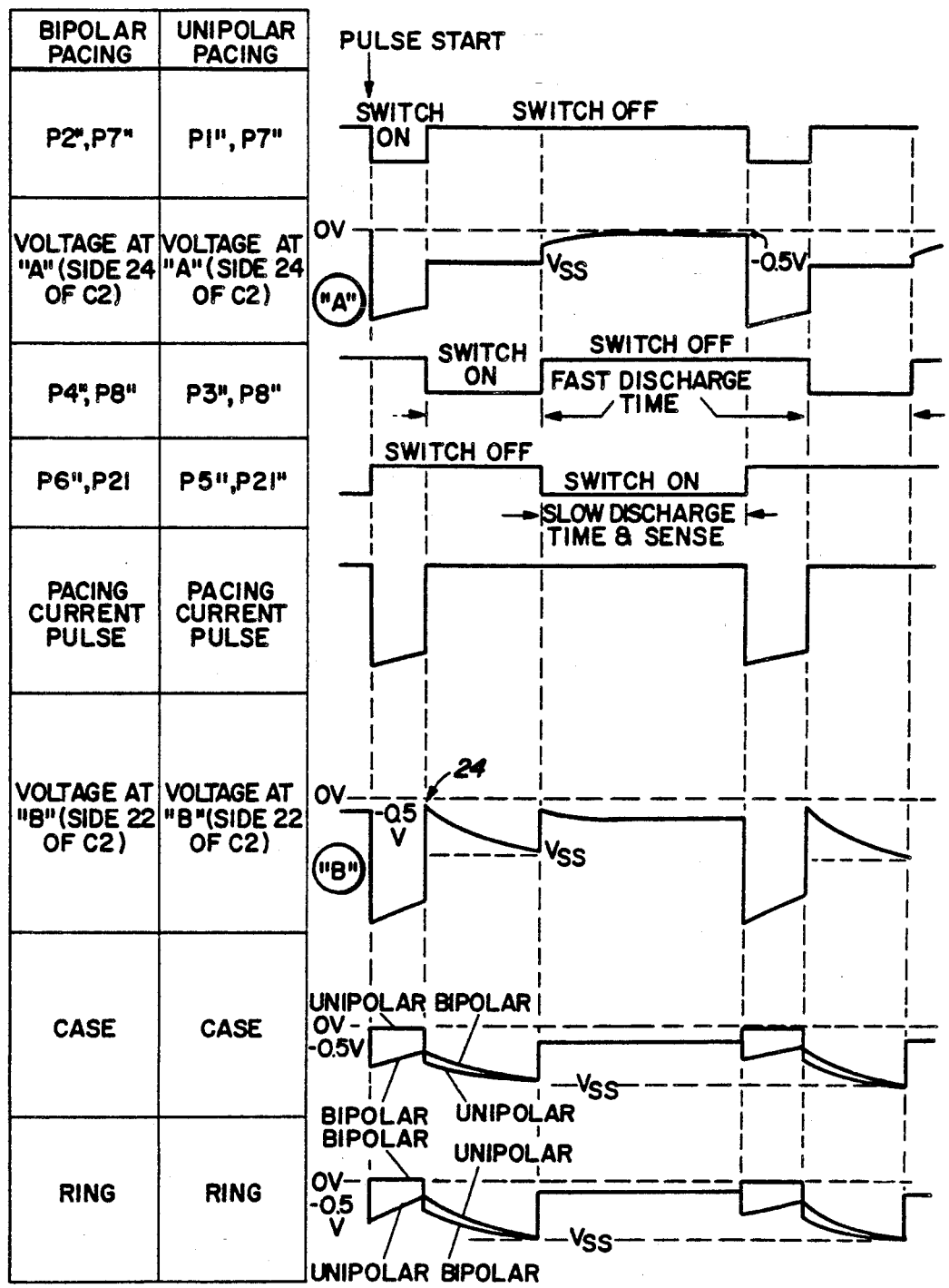
FIG. 2 is a timing diagram illustrating the operation of the pacing portion of the circuit of FIG. 1.

FIG. 2 depicts a simplified timing diagram illustrating the operation of the circuit of FIG. 1. Although the description that follows assumes that a unipolar mode of operation has been selected, FIG. 2 also shows the corresponding signals for bipolar mode of operation. To illustrate how voltages are maintained below $V_{dd}$ and $V_{ss}$, FIG. 2 shows the voltage amplitudes of selected signals when the amplitude of the stimulation pulse is much greater than the available battery voltage ($V_{ss}$), for example, when the amplitude of the stimulation pulse is 3 $V_{ss}$. In FIG. 2, the logic signals P1"–P8" and P21" shown in FIG. 2 are used to respectively control PMOS switches P1–P8, and P21 of FIG. 1. A low level signal turns the switch on (closes the switch), while a high level signal turns the switch off (opens the switch).

As can be seen from FIG. 2, the closure of switches P7 and P1, for unipolar operation, causes the voltage V1 present on capacitor C1 to be applied across terminals 16 and 18. In turn, this causes a pacing current pulse to flow assuming that the tip electrode 16 and the case electrode 18 are in contact with conductive body tissue (or some other load). The waveform identified as "A" in FIG. 2 corresponds to the voltage waveform appearing at point "A" in FIG. 1, which point or node corresponds to the proximal side 24 of capacitor C2. This waveform "A" initially drops to voltage V1 when switch P7 is closed. As soon as P1 and P7 open, switch P3 and switch P8 close to begin the fast discharge time, thereby disconnecting the case electrode 18 from $V_{DD}$. During this fast discharge time, most of the charge remaining on side 24 of capacitor C2 is discharged through switch P3. Hence, as shown in FIG. 2, at the conclusion of the pacing pulse (when P7 and P1 open and P3 and P8 close), the fast discharge time begins and the voltage waveform "A" rises to $V_{SS}$.

Following the fast discharge, a slow discharge time begins and the pacemaker must be ready to sense signals appearing at the tip and/or ring electrode. Hence, switch P21 closes, thereby connecting the case electrode 18 to −0.5V, and switch P5 also closes, thereby providing a slow discharge path through resistor R1 and switch P5 for unipolar mode. This additional slow discharge time ensures that essentially all remaining charge on capacitor C2 is removed before the next pacing pulse is generated. Hence, waveform "A" slowly rises to the −0.5V level during the slow discharge time. Before the next pacing pulse is generated, capacitor C2 has essentially discharged. Just after the end of the fast discharge period, a short auto zero pulse of approximately 100 microseconds is used to discharge capacitor C5 through switch P30 to further ensure that any charge on capacitor C5 is removed.

Also shown in FIG. 2 is the voltage waveform appearing at the distal side 22 of coupling capacitor C2. This voltage is identified as waveform "B". Initially, this voltage is at −0.5 volts, the reference level that is applied to the case during sensing. During the pacing pulse, this voltage goes negative as it follows the negative voltage applied to the proximal side 24 of C2. After the pacing pulse, this voltage attempts to go positive, but by connecting the proximal side 24 of C2 to $V_{SS}$ at this time, this voltage does not go above $V_{DD}$, its most positive point 29, waveform "B" advantageously remains below $V_{DD}$. It may be readily appreciated that if the case was simply connected to $V_{DD}$ prior to a stimulation pulse, the waveform at point 29 would go above $V_{DD}$. Furthermore, the voltages on the ring electrode would also go above $V_{DD}$, due to the bulk conductance of body tissue. During the remaining portion of the fast discharge time, waveform "B" approaches $V_{SS}$, the voltage level applied to the other (proximal) side of capacitor C2. At the end of the fast discharge time, the sense period begins during which the case is connected to −0.5V through P21, and during which time the proximal side of C2 is connected through resistor R1 and P5 to the case. Hence, the distal side of C2 also approaches this same voltage level (−0.5V).

Further shown in FIG. 2 is the case voltage. As can be seen, and as explained previously, this case voltage is connected to $V_{DD}$ (0V) during the time the pacing pulse is delivered by the closure of switch P1. During the fast discharge time, switch P1 is opened and switches P3 and P8 are closed, disconnecting the case from $V_{DD}$ and connecting the case to $V_{SS}$. However, because of the internal resistance associated with switches P3 and P8, the case voltage does not immediately go to $V_{SS}$, but rather approaches $V_{SS}$. After the fast discharge period, the slow discharge period or sense period begins, during which the case is connected to −0.5V through switch P21.

It is noted that during the fast discharge time period, the equivalent circuit for the pacemaker and lead is as shown in FIG. 2A. In FIG. 2A, resistance $R_{p3}$ is the resistance of switch P3 when closed (approximately 100 ohms); capacitance $C_e$ is the tip equivalent capacitance; resistance $R_{e1}$ is the tip equivalent resistance; and resistance $R_{e2}$ is the equivalent case, body return resistance. Typically, for a properly positioned tip electrode, $R_{e1}$ plus $R_{e2}$ will be equal to around 500 ohms. During fast discharge, the case terminal 18 is not directly connected to any pacer voltage source. Hence, case 18 assumes a voltage determined by the voltage on the distal side 22 of capacitor C2 and by the voltage divider comprising $R_{p3}$, $R_{e1}$ and $R_{e2}$ (unipolar operation) or $R_{p4}$ (resistance of switch P4), $R_{e1}$, and $R_{e2}$ (bipolar operation). Mathematically, this case voltage can be expressed as $$\text{CASE VOLTAGE} = V_{SS} + (C2 \text{ voltage}) \frac{R_{p3}}{R_{p3} + (R_{e1} + R_{e2})}$$

At the end of the fast discharge period, it is thus seen that the case voltage will approach $V_{SS}$ (because the C2 voltage approaches zero).

To illustrate how the voltages on the ring electrode are maintained below $V_{DD}$, the ring voltages are also shown in FIG. 2 for unipolar and bipolar operation. Prior to a stimulation pulse the ring and the case are biased to −0.5 volts. During a unipolar output pulse when the case is approximately $V_{DD}$ (less small voltage losses in the switches), the ring electrode is floating. When the case is connected to $V_{SS}$ during a unipolar fast discharge phase, the ring electrode voltage is also approximately $V_{SS}$ due to the 30 bulk conductance of the patient's heart. (Likewise, during a bipolar output pulse, the ring electrode is approximately $V_{DD}$ and the case is floating. During a bipolar fast discharge phase, the ring is connected to $V_{SS}$ through switches P8 and P4 and the case voltage is approximately $V_{SS}$ due to the bulk conductance of the patient's heart.) During the slow discharge, both the ring and the case are again biased to −0.5 volts.

Figure 3:
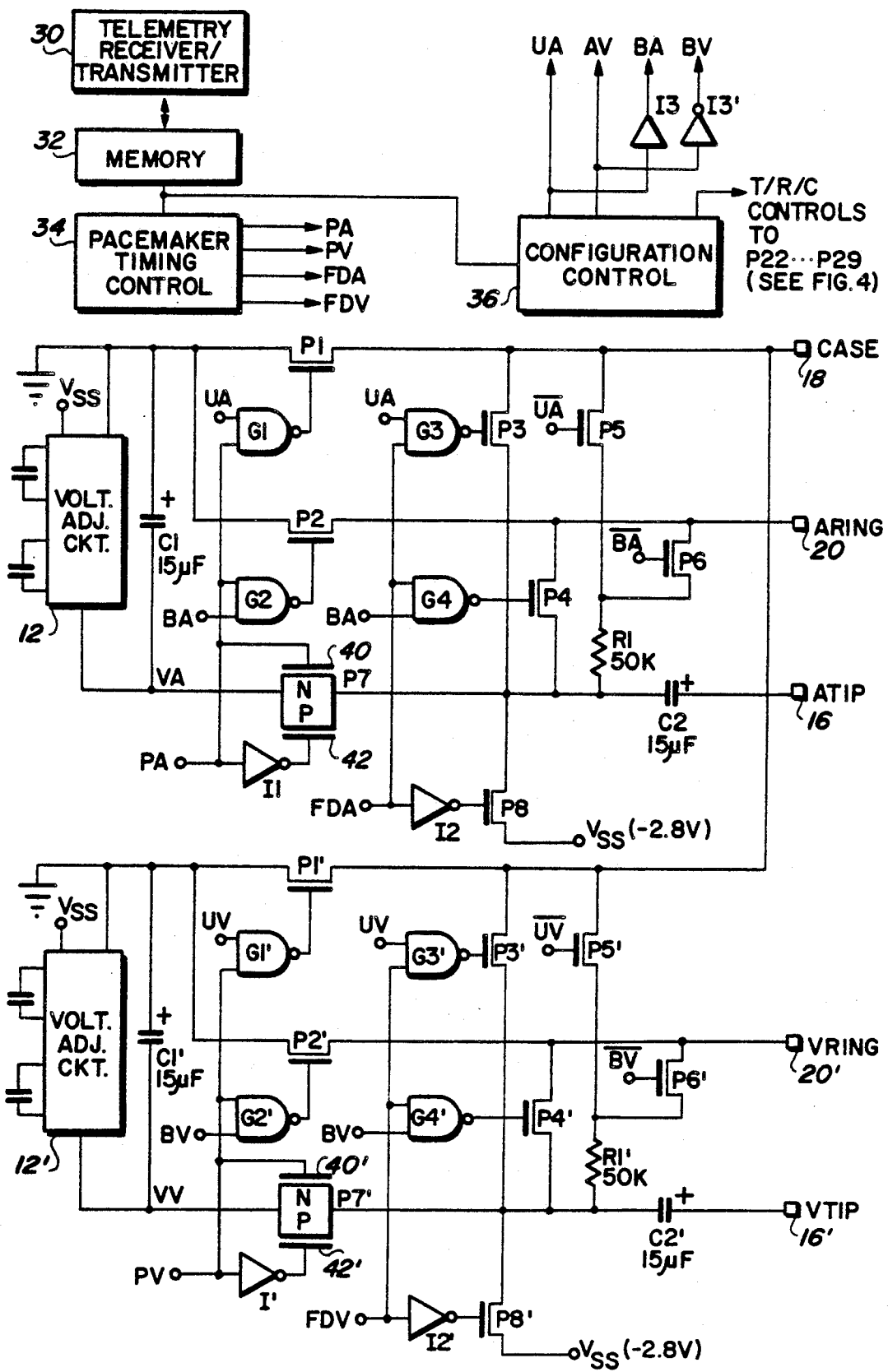
FIG. 3 is a schematic diagram depicting two channels of the pacing or output portion of the present invention.

Referring next to FIG. 3, a more detailed schematic diagram of the pacing portion of the present invention is shown. Many of the elements or parts shown in FIG. 3 correspond to the same elements shown in FIG. 1. Hence, the same numerals or letters are used to identify such elements.

The pacemaker of the present invention includes telemetry receiving and transmitting circuitry 30. Such circuitry may be of conventional design. For example, U.S. Pat. No. 4,223,679 by Schulman et al. describes one such telemetry circuit, which patent is hereby incorporated herein by reference. Telemetry circuit 30 is used to provide two-way communication between an external programmer and the pacemaker once it is implanted in a patient. Externally programmable pacemakers are known; see, for example U.S. Pat. No. 4,232,679 by Schulman and U.S. Pat. No. 4,559,947 by Renger et al., which patents are hereby incorporated herein by reference. Such two-way communication not only allows the pacemaker parameters to be programmed after pacemaker implant, but also allows signals sensed by the implanted pacemaker, or the operating status of the pacemaker, to be telemetered out of the implanted pacemaker to an external receiver.

Further included within the pacemaker is some sort of memory device or element 32. The memory 32 allows the controlling parameters of the pacemaker to be stored so they can provide the needed control for the pacemaker as required. Further, the memory 32 provides a convenient means for realizing any altering or reprogramming of the pacemaker configuration or operating modes. All that needs to be done to make a programming change is to telemeter new controlling data to the appropriate address in the memory 32.

For purposes of the present invention, the operating circuits of the pacemaker include timing control logic 34 and configuration control logic 36. The pacemaker timing control logic 34 generates the signals that control when a pulse is to be provided to the atrium and the ventricle, and when the fast discharge time is to be present for the atrium and the ventricle. These signals are identified as: Pulse Atrium (PA); Pulse Ventricle (PV); Fast Discharge Atrium (FDA); and Fast Discharge Ventricle (FDV). The configuration control logic generates the signals that control whether the pacemaker is to stimulate in a bipolar or unipolar mode. These signals are identified as: Unipolar Atrium (UA); Unipolar Ventricle (UV); Bipolar Atrium (BA); and Bipolar Ventricle (BV). It can be seen from FIG. 3 that signals UA and UV are inverted through inverters I3 and I3' to produce signals BA and BV. This ensures that each channel be either unipolar or bipolar, not both. Further configuration control signals control whether sensing is to be unipolar tip-to-case, unipolar ring-to-case, or bipolar tip-to-ring. These signals are commonly identified as Tip/Ring/Case (T/R/C).

The pacing circuit of FIG. 3 includes two channels, one for pacing the atrium and one for pacing the ventricle. The atrial tip electrode 16 (ATIP) and the ventricular tip electrode 16' (VTIP) are each connected to the tip electrode of a conventional pacing lead, not shown, thereby enabling the pacing pulse to be delivered to the heart. The return path for the stimulating pulse is provided either through the case terminal 18 for unipolar pacing, or the ring electrodes 20 and 20' corresponding to the atrium and the ventricle. Only one case electrode 18 is shown because the case is common to both channels. The discussion that follows is directed to the atrial channel, but applies equally well to the ventricular channel inasmuch as the circuits for both channels, for purposes of the present invention, function the same. For simplicity, like elements in the ventricular channel are numbered similarly using primed notation (i.e., ventricular switch P1' corresponds to atrial switch P1, etc.).

The switches shown in FIG. 3 are realized with MOS switching devices, each gate terminal of which is controlled from logic gates. For example, switch P1 of FIG. 3 is a switch which is normally open unless a low level signal appears at the output of logic gate G1. As the gate G1 is a two-input NAND gate having one input connected to the UA signal and the other connected to the PA signal, it is seen that switch P1 will close only in the presence of a UA and PA signal. Similarly, it is seen that gate G2 will close only in the presence of a BA and PA signal.

Switch P7 of FIG. 1 is realized in FIG. 3, with transmission gates P7 and P7' corresponding to the atrial and ventricular channels. Transmission gate P7 comprises an NMOS switch 40 and a PMOS switch 42 in parallel. A low level logic signal applied to the gate of PMOS switch 42 closes PMOS switch 42, while a high level logic signal applied to the gates of NMOS switch 40 closes NMOS switch 40. Inverter I1 assures that complementary signals are always applied to both sides of this switch, thereby assuring that the switch is either fully on or fully off. A dual switch is employed in this one position because the output voltage can be programmed to any desired value. For example, if the programmed output voltage, VA, is $-0.5V$, then PMOS switch 42 will work properly. However, if the programmed output voltage is close to $-V_{SS}$, the NMOS switch 40 will still work properly (which NMOS switch is turned on by a positive gate voltage, rather than the negative gate voltage used to turn on a PMOS transistor). Hence, the P7 switch configuration assures that this switch will close regardless of the programmed value of VA.

The operation of the pacing circuit of FIG. 3 parallels the operation described above of the circuit of FIG. 1, as explained using the timing diagram of FIG. 2. It is noted that during the fast discharge time period, capacitor C2 is connected to the negative battery potential $V_{SS}$. After the fast discharge period, resistor R1, connected through P5 or P6 (depending upon whether unipolar or bipolar pacing is selected) continues to discharge capacitor C2 at a lower rate.

As indicated, the ventricle channel circuits, comprising the circuits in the lower half of the schematic diagram of FIG. 3, function the same as the atrial channel circuits described above. It should be understood by those skilled in the art that the control signals UA, PA, FDA, UV, PV and FDV are generated through appropriate level shifting circuits, and that inverter gates I1-I3 and I1'-I3', logic gates G1-G4 and G1'-G4' have their positive supply terminals connected to $V_{DD}$, and their negative supply terminals connected to an appropriate supply voltage that is equal to the negative peak of the delivered pulse. This negative voltage can be taken from the same voltage adjusting circuits used to generate the V1 voltage for the pacing pulse, from the storage capacitors C1 or C1', or from any other negative source. This separate supply voltage for these particular gates is required to maintain the switches ON while their respective drain or source terminals go below the negative battery voltage, $V_{SS}$. Also, a larger (in absolute value) gate voltage applied to all of the P switches advantageously allows a reduction in the overall physical dimensions of the devices while maintaining the same ON resistance.

Figure 4:
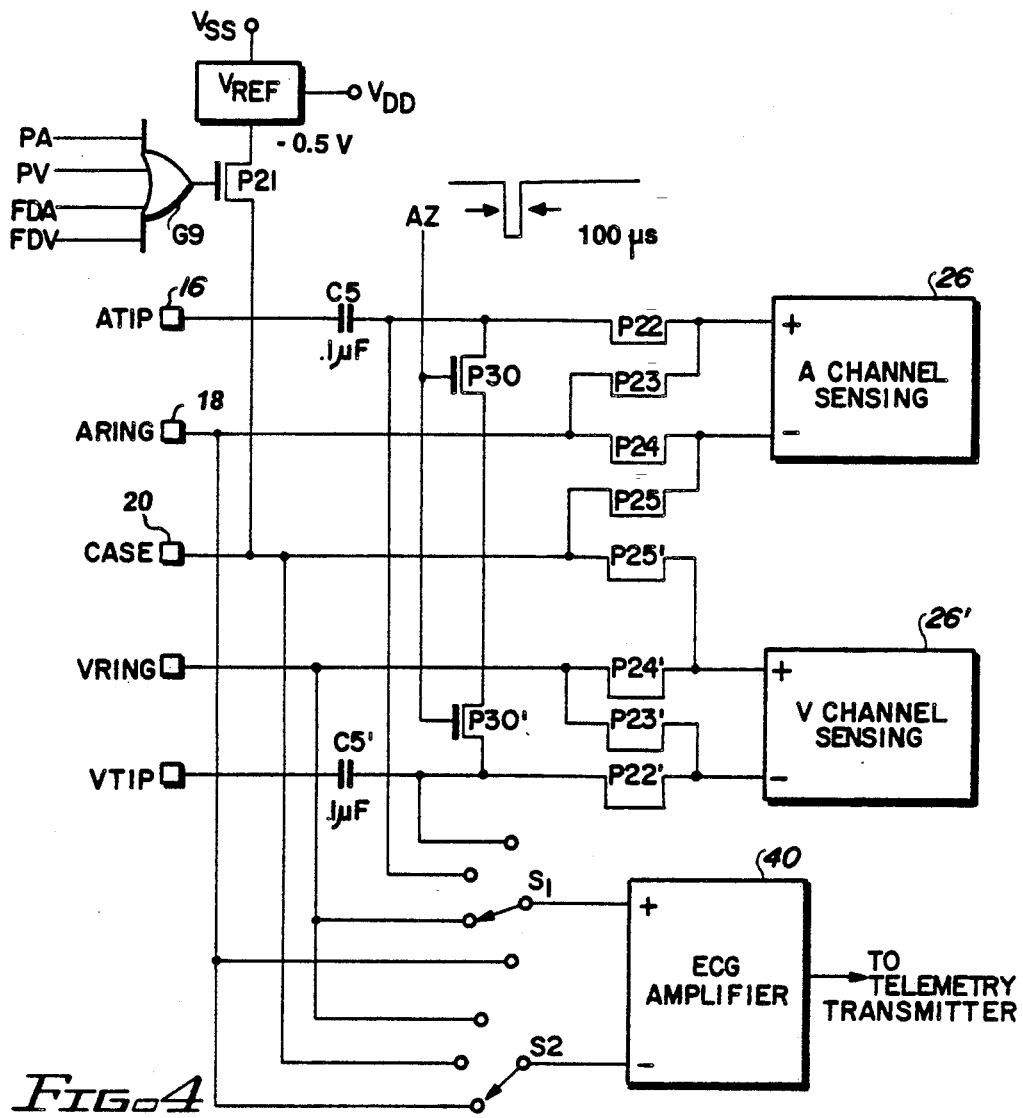
FIG. 4 is a schematic diagram of the sensing portion of the present invention.

Referring next to FIG. 4, it is seen that there are two channel sensing amplifiers or circuits 26 and 26' for sensing millivolt-level signals generated in the atrium and the ventricle, respectively. Eight switching PMOS transistors, P22-P25 and P22'-P25', are controlled by sensing configuration stored data as set forth in FIG. 5. As indicated in FIGS. 4 and 5, each channel can be programmed to sense unipolarly using the tip and case, unipolarly using the ring and case, or bipolarly using the tip and ring. It is noted that during the delivery of a pacing pulse, or during the fast discharge time period, of any channel, switches P22-P25 and P22'-P25' are switched OFF (open or very high impedance) to avoid saturating the sensing circuits 26 and 26'. If no pulse is delivered, and if no fast discharge occurs, gate G9 controls switch P21 to turn it ON (closed or low resistance), connecting the case during sensing to $-0.5$ volts. This action allows some polarization as high as $+0.5$ volts on the ring electrodes without switches P23, P24, P23' or P24' going above $V_{DD}$. It is noted that while $-0.5$ volts is the preferred voltage for connecting the case during sensing, it is only representative of one of a range of voltages that could be so used. For example, any voltage lying within the range of $-0.2$ to $-1.0$ volts could be used for this same purpose.

Still referring to FIG. 4, it is noted that two coupling capacitors, C5 and C5', prevent applying the voltages remaining on capacitors C2 and C2', after fast discharge, to P22 or P22'. As noted in FIG. 2, waveform "A", it is possible that some voltage will remain on capacitors C2 or C2' at this time (after fast discharge), and this voltage could saturate the sensing circuits 26 and 26'. Accordingly, capacitors C5 and C5' are used to prevent such saturation from occurring. To further ensure that any charge on capacitors C5 and C5' is removed, a short auto zero pulse of approximately 100 microseconds is used to discharge capacitors C5 and C5' through switches P30 and P30', respectively, just after the end of the fast discharge period. As seen in FIG. 4, switches P30 and P30' connect the proximal side of capacitors C5 and C5' to the case 18, which in turn is connected through switch P21 to $-0.5$ volts. This sensing configuration prevents any switch voltage from going above $V_{DD}$. During sensing, all of the switch voltages remain around $-0.5$ volts.

As is further shown in FIG. 4, one-pole switches S1 and S2 may also optionally be used to connect the input of an ECG amplifier 40 to the signals that are sensed through the tip and ring electrodes. Such signals comprise the intercardiac ECG signals that can then be processed and telemetered to an external receiver.

While the invention herein disclosed has been described by means of specific embodiments and applications thereof, numerous modifications and variations could be made thereto by those skilled in the art without departing from the spirit and scope of the present invention. It is to be understood therefore that within the scope of the appended claims, the invention may be practiced otherwise than as specifically described herein.

What is claimed is:

1. An implantable pacemaker, comprising: a first electrode terminal;
   a group of return electrode terminals, said group including a second electrode terminal (20) and a third electrode terminal (18);
   means for selecting a return electrode terminal selected from said group of return electrode terminals;
   a voltage source (14) having a ground reference potential ($V_{dd}$) and a negative reference potential ($V_{SS}$) associated therewith;
   means (28), coupled to said voltage source, for generating a first reference potential different from said ground reference potential;
   pulse generating means (12, C1) for generating a stimulation pulse;
   a coupling capacitor (C2) for coupling said stimulation pulse generated by said pulse generating means to said first electrode terminal;
   pacing configuration means for electrically connecting said selected return electrode terminal to said ground reference potential only during said stimulation pulse, and for electrically connecting said first electrode to said pulse generator means so that said stimulation pulse is delivered between said first electrode and said selected return electrode; and
   fast discharge means for discharging said coupling capacitor towards said first reference potential for said prescribed time period by connecting together said coupling capacitor, said selected return electrode, and said first reference potential for a prescribed time period immediately subsequent to said stimulation pulse, whereby said selected return electrode provides a ground reference during said stimulation pulse and a non-ground reference during a fast discharge time period.

2. The implantable pacemaker of claim 1, wherein said pacing configuration means comprises:
   first switch means (P7) for selectively connecting said pulse generating means to said first electrode terminal (16) through said coupling capacitor;
   second switch means (P1) for selectively connecting said ground reference potential to said third electrode terminal (18);
   third switch means (P2) for selectively connecting said ground reference potential to said second electrode terminal (20); and
   control means for generating control signals that control the operation of said first, second and third switching means.

3. The implantable pacemaker of claim 1, wherein said first reference potential is a negative potential corresponding to said negative reference potential ($V_{ss}$) of said voltage source.

4. The implantable pacemaker of claim 1, further comprising:
   control means for generating a timed sequence of control signals; and
   slow discharge means for discharging said coupling capacitor in response to said timed sequence of control signals generated by said control means.

5. The implantable pacemaker of claim 1, wherein said slow discharge means comprises:
   a resistor (R1) connected in series with said coupling capacitor and said selected return electrode.

6. An implantable pacemaker, comprising:
   a tip electrode terminal (16);
   a group of return electrode terminals, said group including a ring electrode terminal (20) and a case electrode terminal (18);
   means for selecting a return electrode terminal from said group of return electrode terminals;
   a battery (14) having a positive voltage terminal ($V_{DD}$) and a negative voltage terminal ($V_{SS}$), a prescribed one of said positive or negative voltage terminals comprises a ground reference potential;
   pulse generating means (12, C1) for generating a stimulation pulse;
   placing configuration means for electrically connecting said selected return electrode terminal to said ground reference potential only during said stimulation pulse, and for electrically connecting said tip electrode to said pulse generator means so that said stimulation pulse is delivered between said tip electrode and said selected return electrode being selected from a group of said case and said second electrode;
   sensing means (26), having a first and second input terminal, for sensing electrical signals therebetween; and
   programming means for programming an electrode configuration for said sensing means, said electrode configuration including at least two of said case electrode terminal, first electrode terminal and second electrode terminals; and
   sensing configuration means for electrically connecting said sensing means to at least two of said case electrode terminal, first electrode terminal and second electrode terminal in accordance with said programming means.

7. The implantable pacemaker of claim 6, wherein said pacing configuration means comprises:
   first switch means (P7) for selectively connecting said pulse generating means to said tip electrode terminal (16);
   second switch means (P1) for selectively connecting said ground reference potential to said case electrode terminal (18);
   third switch means (P2) for selectively connecting said ground reference potential to said ring electrode terminal (20); and
   control means for generating control signals that control operation of said first, second and third switching means.

8. The implantable pacemaker of claim 7, wherein said electrode configuration comprises a first and a second electrode terminal, said first electrode terminal being selected from one of said tip and said ring electrode terminals, and said second electrode terminal being selected from one of said case and ring electrode terminals, wherein said sensing configuration means comprises:
   fourth switch means (P22, P23) for connecting said first electrode terminal to said first input terminal of said sensing means; and
   fifth switching means (P24, P25) for connecting said second electrode terminal to said second input terminal of said sensing means;

wherein said control means further controls operation of said fourth and fifth switching means.

9. The implantable pacemaker of claim 8, further comprising:
a coupling capacitor (C2) having a distal side and a proximal side, said distal side being connected to said tip electrode terminal;
fast discharge means for connecting together said proximal side of said coupling capacitor, said selected return electrode, and said negative voltage terminal of said battery, said connecting being performed in response to control signals generated by said control means, whereby said coupling capacitor is discharged rapidly to the potential of said negative voltage terminal of said battery.

10. The implantable pacemaker of claim 9, wherein said control means comprises:
timing means for generating said control signals in a timed sequence that causes said first switch means and said fast discharge means to perform their respective connections sequentially.

11. The implantable pacemaker of claim 10, further comprising:
a resistor (R1) connected in series with said coupling capacitor and said selected return electrode terminal; and
slow discharge means for discharging said coupling capacitor through said resistor in response to said timed sequence control signals generated by said control means.

12. The implantable pacemaker of claim 8, further comprising:
means (28), coupled to said battery, for generating a first reference potential different from said ground reference potential; and
means for biasing said fourth and fifth switching means to said first reference potential.

13. The implantable pacemaker of claim 12, wherein said biasing means comprises:
a coupling capacitor (C5) having a distal side connected to said tip electrode terminal and a proximal side connected to said fourth switching means;
sixth switching means (P21) for electrically connecting said case to said first reference potential during operation of said sensing means; and
seventh switching means (P30), for connecting said proximal side of said coupling capacitor to said case electrode terminal for a short prescribed time period prior to the operation of said sensing means, wherein said control means further includes generating control signals for controlling said sixth and seventh switching means.

14. The implantable pacemaker of claim 13, wherein said short prescribed time period comprises 50 to 150 microseconds.

15. The implantable pacemaker of claim 12, wherein said first reference potential generated by said reference voltage generator is between −0.2 and −1.0 volts.

16. An implantable pacemaker, for coupling to an implantable lead, comprising:
a stimulating electrode terminal for coupling to the tip electrode of said implantable lead;
a reference terminal;
a voltage source having a ground potential and a first voltage potential ($V_{SS}$) associated therewith;
pulse generator means for generating a stimulation pulse, said pulse generator means comprising a storage capacitor, a first side of said storage capacitor being connected to said ground potential, and charge means for charging said storage capacitor from said voltage source;
control means for generating a first control signal having a first pulse width and a second control signal having a second pulse width, said second control signal being generated immediately subsequent to said first control signal;
a coupling capacitor having a distal side and a proximal side, said distal side being connected to said stimulating electrode terminal;
first switch means for connecting said proximal side of said coupling capacitor to a second side of said storage capacitor in response to said first control signal;
second switch means for connecting said reference terminal to said ground potential in response to said first control signal, whereby a stimulation pulse is delivered to the patient's heart through said coupling capacitor in response to said first control signal; and
third switch means for connecting together said proximal side of said coupling capacitor, said reference terminal, and said first voltage potential in response to said second control signal, whereby said coupling capacitor discharges to said first voltage potential during said prescribed time period generated by said control means.

17. The pacemaker of claim 16, wherein said implantable lead includes a ring electrode proximal to said tip electrode and said pacemaker further includes a pacemaker case, said pacemaker further comprising:
means for selectively coupling said reference terminal to one of said pacemaker case and said ring electrode of said implantable lead.

18. The pacemaker of claim 17 wherein said control means includes means for generating a third control signal, said pacemaker further comprises:
a voltage reference generator, coupled to said voltage source, for generating a second reference potential;
timing means for generating a timing cycle, said timing cycle having a pacing time interval and a sensing time interval;
sensing means, having a first and second input terminal, for sensing cardiac signals during said sensing time interval; and
fourth switch means for connecting said pacemaker case to said second reference potential in response to said third control signal generated by said control means during said sensing time interval.

19. The sense amplifier of claim 18, wherein said control means includes means for generating a fourth control signal, further comprising:
a second coupling capacitor (C5( connected between said stimulating electrode terminal and said first input terminal of said sensing means; and
fifth switching means (P21), responsive to said fourth control signal, for selectively connecting said pacemaker case to said second reference potential generated by said voltage reference generator means when operating in said sensing mode of operation.

20. The pacemaker of claim 19, wherein said second reference potential is a potential that is no more than 1.0 volt in magnitude as measure width respect to said ground potential.

21. The pacemaker of claim 20, wherein said second reference potential is a negative potential with respect to said ground potential.

22. The pacemaker of claim 21, wherein said second reference potential is approximately −0.5 volts.

23. An implantable pacemaker, comprising:
pacing means for generating a stimulating pulse;
sensing means for sensing cardiac signals;
battery means for providing operating power and first and second voltage reference potentials;
timing means for generating a timing cycle, said timing cycle having a pacing time interval and a sensing time interval;
a tip electrode terminal and a reference electrode terminal for delivering said stimulating pulse from said pacing means during said pacing time interval and for delivering cardiac signals to said sensing means during said sensing time interval; and
switching means for connecting said reference electrode terminal to said first voltage reference potential during said pacing time interval, and for connecting said reference electrode terminal to said second voltage reference potential during said sensing time interval.

24. The pacemaker of claim 23, wherein said first voltage reference potential is the most positive voltage reference potential available from said battery means, and said second voltage reference potential is a voltage reference potential that is 0.2 to 1.0 volts less than said first voltage reference potential.

25. The pacemaker of claim 23, further comprising a voltage reference generator, coupled to said battery, for generating a third voltage reference potential, said pacemaker further comprising:
a coupling capacitor for coupling said pacing means to said tip electrode terminal;
fast discharge means for connecting said coupling capacitor to said third voltage reference potential for a fast discharge time period immediately following the delivery of said stimulating pulse through said coupling capacitor; and
means for switching said reference electrode terminal from said first voltage reference potential to said third voltage potential during said fast discharge time period.

26. The pacemaker of claim 25, wherein said third voltage reference potential is the most negative voltage potential available from said battery means.

27. The implantable pacemaker of claim 25, further comprising a pacemaker case, wherein said reference electrode terminal is said pacemaker case.

28. A method of operating a pacemaker in contact with body tissue, said pacemaker including a tip electrode terminal, and a return electrode terminal, said pacemaker further having a pulse generator for generating stimulation pulses through a coupling capacitor to the tip electrode terminal, said pacemaker further having a voltage source for generating a first voltage potential and a second voltage potential, said method comprising the steps of:
(a) generating a first signal having a first time period and a second signal having a second time period following said first time period;
(b) connecting said first voltage potential (V1) of said voltage source to a proximal side (24) of said coupling capacitor in response to said first signal for said first time period;
(c) connecting a second voltage potential ($V_{DD}$) of said voltage source to the return electrode terminal in response to said first signal during said first time period, whereby a stimulating pulse, having a duration equal to said first time period, is delivered through said coupling capacitor to the tip electrode terminal, the tip electrode terminal being connected to a distal side of said coupling capacitor;
(d) disconnecting the return electrode terminal from said second voltage potential ($V_{DD}$) in response to said second signal during said second time period;
(e) connecting said proximal side (24) of said coupling capacitor to a discharge potential ($V_{SS}$) in response to said second signal for said second time period; and
(f) connecting said proximal side (24) of said coupling capacitor to the return electrode terminal in response to said second signal during said second time period.

29. The method of claim 28, wherein said generating step further comprises generating a third signal having a third time period after said second time period, said method further comprising the step of:
(g) connecting said coupling capacitor to the return electrode terminal through a discharge resistor in response to said third signal for said third time period.

30. The method of claim 28, wherein said pacemaker includes a case electrode terminal and a ring electrode terminal, the method further comprising the initial step of:
selecting the return electrode terminal from one of said case electrode terminal and said ring electrode terminal.

31. A method of sensing cardiac signals in a pacemaker, said pacemaker having a case, a tip electrode terminal, and a ring electrode terminal, and said pacemaker further having means for programming modes of operation of said pacemaker, and sensing means coupled to the tip electrode terminal through a coupling capacitor for sensing cardiac signals, said method comprising the steps of:
(a) programmably selecting one of a first, second, and a third sensing mode of operation;
(b) connecting a first input terminal of a sensing means to the tip electrode terminal through a coupling capacitor in response to said first and said second mode of operation, and to the ring electrode terminal in response to said third mode of operation; and
(c) connecting a second input terminal of said sensing means to the ring electrode terminal in response to said first mode of operation, and to the pacemaker case in response to said second and third mode of operation;
whereby cardiac signals in said first mode of operation are sensed between the tip and ring electrode terminal, cardiac signals in said second mode of operation are sensed between the ring electrode terminal and the pacemaker case, and cardiac signals in said third mode of operation are sensed between the ring electrode terminal and the pacemaker case.

32. The method of claim 31, further comprising the steps of:
(d) providing a voltage source having a ground reference potential and a first reference potential;
(e) connecting the case to said first reference potential during said first, second, and third sensing mode of operation so that the ring electrode terminal is also coupled to said first reference potential through bulk conductance of the pantient's heart; and (f) connecting said first reference potential for a brief duration to the first input terminal of a sensing means, whereby the first and second input terminals of said sensing means are biased to said first reference potential so that voltages above said ground reference potential will be eliminated.

33. The method of claim 32, wherein said first reference potential is a reference potential within the range of −0.2 to −1.0 volts.

34. A method of operating a pacemaker, said pacemaker for coupling to a plurality of electrode terminals, the pacemaker further having a pulse generator means, a voltage reference generator, and a sensing means having a first and a second input terminal, said method comprising the steps of:

(a) providing a sensing mode and a pacing mode of operation;
(b) connecting one of said plurality of electrode terminals to said first input terminal of said sensing means during said sensing mode of operation;
(c) connecting one of said plurality of electrode terminals to said second input terminal of said sensing means during said sensing mode of operation;
(d) connecting one of said plurality of electrode terminals to said first reference potential during said sensing mode of operation;
(e) connecting one of said plurality of electrode terminals to said pulse generating means during said pacing mode of operation;
(f) connecting one of said plurality of electrode terminals to provide a return path for said pulse generating means during said pacing mode of operation; and
(g) connecting said return electrode of step (f) to a ground reference potential during said pacing mode of operation, whereby a simulation pulse is generated.

35. The method of operating a pacemaker as recited in claim 34, wherein said plurality of electrode terminals includes a case electrode terminal, and a tip and a ring electrode terminal for coupling to a bipolar lead having a tip and ring electrode, said pacemaker further having electrode terminal selection means, and wherein step (b) comprises:

selecting one of said tip electrode terminal and ring electrode terminal from the plurality of electrode terminals for connection to said first terminal of said sensing means.

36. The method of operating a pacemaker as recited in claim 35, wherein said (c) comprises:

selecting one of said ring electrode terminal or said case electrode terminal of the pacemaker from the plurality of electrode terminals for connection to said second terminal of said sensing means.

37. The method of claim 34, wherein said first reference potential is a reference potential within the range of −0.2 to −1.0 volts.

38. The method of claim 34, wherein said pacemaker further includes memory means, and solid state switch means responsive to the data stored in said memory means for switching which occurs in steps (b), (c), and (d), said method further comprises the steps of:

storing programming data in said memory means; and
controlling the solid state switch means with said stored programming data, whereby said programming data is used to select the selected sense and return electrodes.

39. A method of configuring a pacemaker, said pacemaker including first and second electrode terminals, and a voltage source having positive and negative voltage terminals, said pacemaker having a timing means for generating a pacing time interval and a sensing time interval, said method comprising the steps of:

(a) generating a voltage reference potential;
(b) generating a stimulation pulse during said pacing time interval between said first electrode terminal and said second electrode terminal;
(c) connecting said second electrode terminal of said pacemaker to said positive voltage terminals of said voltage source during said pacing pacing time interval; and
(d) connecting said second electrode terminal of said pacemaker to said voltage reference potential during said sensing time interval.

40. The method of claim 39, wherein said timing means further is for generating a discharge time period immediately following said pacing time period, the method further comprising:

connecting said second electrode terminal of said pacemaker to said negative voltage terminal of said voltage source during said discharge time period.

41. The method of claim 40, wherein said voltage reference potential is 0.2 to 1.0 volts less than the voltage available at said positive voltage terminal during said sensing mode of operation.

42. A system for configuring a pacemaker, said system comprising:

pulse generator means for generating a stimulation pulse;
sensing means for sensing cardiac signals;
a tip and a return electrode terminal, for delivering stimulating pulses generated by said pulse generator means and for delivering said cardiac signals to said sensing means;
a voltage source having positive and negative voltages terminals;
means for generating a voltage reference potential different from the voltage potential available at said positive and negative voltage terminals;
timing and control means for generating a pacemaker timing cycle, the timing cycle having a pacing time interval during which said stimulating pulse is delivered, a discharge time interval immediately following said pacing time interval, and a sensing time interval for sensing cardiac signals;
means for connecting said return electrode terminal to said positive voltage terminal of said voltage source during said pacing interval;
means for connecting said return electrode terminal to said negative voltage terminal of said voltage source during said discharge time interval; and
means for connecting said return electrode terminal to said voltage reference potential during said sensing mode of operation.

43. The system of configuring a pacemaker of claim 42, further comprising:

a case for housing said pulse generator means, said sensing means, and said voltage source; and wherein said return electrode terminal is connected to said case.

44. The system of configuring a pacemaker of claim 42, further comprising:

a lead, having a tip electrode and a ring electrode, for coupling between the pacemaker and the patient's heart, wherein said tip electrode terminal of the pacemaker is capable of being coupled to said tip electrode of said lead and said return electrode terminal of the pacemaker is capable of being coupled to said ring electrode of said lead.

45. The system of configuring a pacemaker of claim 42, further comprising:

a case for housing said pulse generator means, said sensing means, and said voltage source;
a lead, having a tip electrode and a ring electrode, for coupling between the pacemaker and the patient's heart; and
selection means for selecting a return electrode from one of said case and said ring electrode of said lead.

* * * * *

UNITED STATES PATENT AND TRADEMARK OFFICE
CERTIFICATE OF CORRECTION

PATENT NO. : 4,991,583
DATED : 2/12/91
INVENTOR(S) : Sergiu Silvian

It is certified that error appears in the above-indentified patent and that said Letters Patent is hereby corrected as shown below:

On column 14, line 24, delete "being selected from a group of said case and said second electrode" and insert therefor --terminal--.

On column 14, line 29, delete "and".

On column 14, line 33, delete "first" and insert therefor --tip--.

On column 14, line 34, delete "second electrode terminals" and insert therefor --ring electrode terminal--.

On column 14, line 37, delete "first" and insert therefor --tip--.

On column 14, line 38, delete "second" and insert therefor --ring --.

On column 18 line 35, delete "coupled to the tip electrode terminal through a coupling capacitor".

On column 18, line 41, delete "a" and insert therefor --said--.

On column 18, line 55, delete "ring" and insert therefor --tip--.

UNITED STATES PATENT AND TRADEMARK OFFICE
CERTIFICATE OF CORRECTION

PATENT NO. : 4,991,583
DATED : 2/12/91
INVENTOR(S) : Sergiu Silvian

It is certified that error appears in the above-indentified patent and that said Letters Patent is hereby corrected as shown below:

On Column 14, line 18, delete "placing configuration" and insert therefor --pacing configuration--.

Signed and Sealed this

Twelfth Day of October, 1993

Attest:

BRUCE LEHMAN

*Attesting Officer*   Commissioner of Patents and Trademarks